(12) United States Patent
Tets et al.

(10) Patent No.: US 10,098,899 B2
(45) Date of Patent: *Oct. 16, 2018

(54) DRUG WITH ACTIVITY AGAINST THE HERPES VIRUS FAMILY

(71) Applicants: Viktor Veniaminovich Tets, St. Petersburg (RU); Georgy Viktorovich Tets, St. Petersburg (RU)

(72) Inventors: Viktor Veniaminovich Tets, St. Petersburg (RU); Georgy Viktorovich Tets, St. Petersburg (RU); Viktor Iosifovich Krutikov, St. Petersburg (RU)

(73) Assignees: Viktor Veniaminovich Tets, Saint-Petersburg (RU); Georgy Viktorovich Tets, Saint-Petersburg (RU)

( * ) Notice: Subject to any disclaimer, the term of this patent is extended or adjusted under 35 U.S.C. 154(b) by 0 days.

This patent is subject to a terminal disclaimer.

(21) Appl. No.: 15/389,909

(22) Filed: Dec. 23, 2016

(65) Prior Publication Data

US 2017/0232010 A1    Aug. 17, 2017

Related U.S. Application Data

(63) Continuation of application No. 13/976,028, filed as application No. PCT/RU2011/000060 on Jan. 28, 2011, now Pat. No. 9,567,295.

(30) Foreign Application Priority Data

Dec. 27, 2010    (RU) ................................ 2010153852

(51) Int. Cl.
A61K 31/63    (2006.01)

(52) U.S. Cl.
CPC .................................... *A61K 31/63* (2013.01)

(58) Field of Classification Search
None
See application file for complete search history.

(56) References Cited

U.S. PATENT DOCUMENTS

| | | |
|---|---|---|
| 6,417,181 B1 | 7/2002 | Bender et al. |
| 6,569,864 B1 | 5/2003 | Douglas et al. |
| 2003/0086992 A1 | 5/2003 | Tanaka |
| 2004/0157848 A1 | 8/2004 | Maziasz |
| 2005/0037032 A1 | 2/2005 | Catania et al. |
| 2013/0287841 A1 | 10/2013 | Tets et al. |

FOREIGN PATENT DOCUMENTS

| | | |
|---|---|---|
| DE | 3544409 A1 | 10/1986 |
| DE | 10210319 A1 | 9/2003 |
| EP | 1038868 A2 | 9/2000 |
| EP | 1136472 A1 | 9/2001 |
| EP | 2659891 A1 | 11/2013 |
| RU | 1405269 | 12/1993 |
| RU | 21802828 C1 | 5/2002 |
| RU | 2199526 C2 | 2/2003 |
| RU | 2373951 C1 | 11/2009 |
| RU | 2452490 C1 | 6/2012 |
| WO | 2000/034234 A1 | 6/2000 |
| WO | 2012091610 A1 | 7/2012 |

OTHER PUBLICATIONS

Pharmaceutical Salts: Properties, Selection, and Use (p. 331)(Stahl et al., Ed.)(2002).*
English translation (2014) of RU 2199526 (2003).*
Rothaus (NEJM Resident 360 (Aug. 18, 2016))(retrieved from <https://resident360.nejm.org/content_items/genital-herpes> on Jun. 24, 2017).*
International Preliminary Report on Patentability Issued in International Application No. PCT/RU2014/000420 dated Oct. 12, 2015 and English Translation Thereof, 9 pages.
Supplemental/Extended European Search Report Issued in European Patent Application No. 14806838.0 dated Jan. 13, 2017, 9 pages.
International Search Report and Written Opinion dated Sep. 25, 2014, Issued in International Application No. PCT/RU2014/000420. (translation included).
International Search Report and Written Opinion dated Sep. 29, 2011, Issued in International Application No. PCT/RU2011/000060. (translation included).
Noueiry et al., "Identification of novel small-molecule inhibitors of west nile virus infection", Journal of Virology, vol. 81, No. 21, 2007, pp. 11992-12004.

(Continued)

*Primary Examiner* — Patricia Duffy
*Assistant Examiner* — Garen Gotfredson
(74) *Attorney, Agent, or Firm* — Troutman Sanders LLP

(57) ABSTRACT

The invention relates to medicine, and specifically to synthetic biologically active derivatives of carbopentoxysulfanilic acid. The novel substance comprises a (2,6-dichlorophenyl)amide salt of carbopentoxysulfanilic acid of general formula:

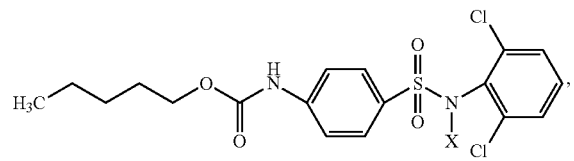

Where X is Na, K, NH$_4$; the drug may be contained in tablets, including sublingual tablets, or in capsules, or in suppositories, or in drops, or in mixtures, or in ointments, creams or other forms for application to the skin and mucosae, or in an oral-buccal film, or in a spray, or in a liquid for parenteral administration, or in chewing gum. A preparation having pronounced activity against herpes viruses is thus produced.

20 Claims, No Drawings

(56) References Cited

OTHER PUBLICATIONS

Didkovskii et al., "Gerpes—virusnaya infekstiya: Klinicheskoe znachenie i printsipy terapii", Russkii Meditsinskii Zhurnal, 2004, vol. 12, No. 7, pp. 459-464.
Furman et al., "Aciclovir-resistant mutants of herpes simplex virus type 1 express altered DNA polymerase or reduced aciclovir phosphorylating activities", J. Virol., 1981, vol. 3, pp. 936-941.
Extended European Search Report Issued in European Application No. 11853372.8, dated Dec. 10, 2013.
Mashkovskiy, Lekarstvenniye Sredstva, Moscow 2001, vol. 2, pp. 321-334.
International Preliminary Report on Patentability Issued in corresponding International Application No. PCT/RU2011/000060. (translation included).
Berge et al., Journal of Pharmaceutical Sciences, vol. 66, Issue 1 (1977).
International Preliminary Report on Patentability issued by the International Searching Authority in International Application No. PCT/RU2016/000624 dated Mar. 20, 2018.
International Search Report issued by the International Searching Authority in International Application No. PCT/RU2016/000624 dated Mar. 6, 2017.
Written Opinion issued by the International Searching Authority in International Application No. PCT/RU2016/000624 dated Mar. 6, 2017.

\* cited by examiner

DRUG WITH ACTIVITY AGAINST THE HERPES VIRUS FAMILY

CROSS-REFERENCE TO RELATED APPLICATIONS

This application is a continuation of U.S. patent application Ser. No. 13/976,028, now issued as U.S. Pat. No. 9,567,295, which was filed on Jun. 26, 2013, and is a U.S. National Stage of International Patent Application No. PCT/RU2011/000060, filed on Jan. 28, 2011, which claims priority to Russian Patent Application No. 2010153852, filed on Dec. 27, 2010, all of which applications are herein incorporated by reference in their entirety. The International Application No. PCT/RU2011/000060 published on Jul. 5, 2012 as WO 2012/091610.

TECHNICAL FIELD

The invention relates to medicine, and specifically to synthetic biologically active derivatives of carbopentoxysulfanilic acid.

The inventive substance has pronounced antiviral activity, mainly against various viruses of the herpes family.

It can be used in medicine, veterinary science and cosmetic science for preventing and treating diseases related to the herpes virus family.

BACKGROUND ART

One of the most serious problems of modern medicine consists in virus infections, the majority of which are extremely difficult to treat or even lack an adequate antiviral therapy. Said difficulty is due to insufficient effectiveness of existing preparations and the fast variability of causative agents that leads to emergence of resistant forms (see world wide web medinfo.ru/sovety/derm/02.phtml).

Similar problems exist in veterinary science.

The most popular preparations for treating wide-spread infections caused by herpes simplex virus are aciclovir, a synthetic acyclic analogue of deoxyguanosine, and Famvir (famciclovir), which transforms in the organism into an active antiviral compound penciclovir (see world wide web rlsnet.ru/_mnn_index_id_1843.htm). Each of the abovementioned preparations has certain disadvantages. Aciclovir is less active against type II herpes viruses, famciclovir has an extensive list of contraindications, however the majority of circulating herpes viruses currently are resistant towards these preparations that have been used for a long time (P. A. Furman, D. M. Coen, M. H. St. Clair and P. A. Schaffer Aciclovir-resistant mutants of herpes simplex virus type 1 express altered DNA polymerase or reduced aciclovir phosphorylating activities. J. Virol. 1981 December; 3: 936-941) (a copy of the link is attached).

The most popular antiherpetic preparation—aciclovir—2-amino-1,9-dihydro-9-[(2-hydroxyethoxy)methyl]-6H-purine-6-on has been taken as a prototype, (see world wide web rlsnet.ru/mnn_index_id_290.htm) (a copy of the link is attached):

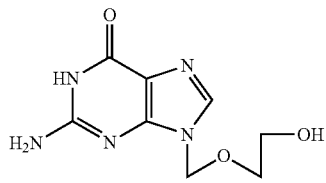

Its disadvantage consists in the abovementioned fact that the majority of herpes viruses have acquired resistance towards this preparation.

It is an object of the present invention to create a preparation having pronounced activity against herpes viruses.

SUMMARY OF THE INVENTION

According to the invention there is provided synthesis of a novel substance that is a (2,6-dichlorophenyl)amide salt of carbopentoxysulfanilic acid of general formula:

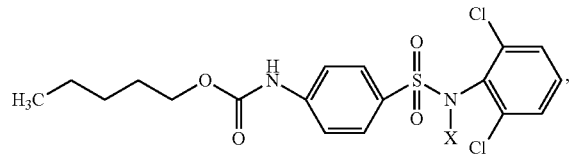

Where X is Na, K, $NH_4$; the drug be contained in tablets, including sublingual tablets, or in capsules, or in suppositories, or in drops, or in mixtures, or in ointments, creams or other forms for application to the skin and mucosae, or in an oral-buccal film, or in a spray, or in a liquid for parental administration, or in chewing gum.

The applicant has not found any sources of information containing data on technical solutions identical to this invention, which enables to conclude that the invention conforms to the criterion "Novelty" (N). The inventive drug exhibits pronounced activity against the larger part of herpes viruses.

The applicant has not found any sources of information containing data on the influence of the features of the invention on the technical result produced by their implementation. In applicant's opinion, this enables to conclude that the present technical solution conforms to the criterion "Inventive Step" (IS).

BRIEF DESCRIPTION OF THE DRAWINGS

The invention is further explained, by way of detailed description of examples of its embodiments, without reference to any drawings.

PREFERRED EMBODIMENT

Synthesis of the inventive substance is performed in several stages.

I. Synthesis of Phenylcarbamic Acid Amyl Ester 8.5 g (0.096 mol) of amyl alcohol were added drop-wise while stirring to 11.5 g (0.096 mol) of phenylisocyanate placed into a beaker. The warming-up of the reaction mass was observed. After 1 hour the mixture solidified in the form of colorless crystals. The output of phenylcarbamic acid amyl ester amounted to approximately 100%.

II. Synthesis of Carbopentoxysulfanilic Acid Chloride 2.07 g (0.010 mol) of phenylcarbamic acid amyl ester were slowly added while stirring to 17.5 g (0.150 mol) of chlorosulfonic acid heated to 30° C., maintaining the temperature of reaction mass not higher than 35° C. Then the mixture was slowly heated to 50° C. and maintained at 50-55° C. for 2 hours. The obtained sulpho mass was poured to ice while stirring, maintaining the temperature not higher than 20° C. The residue was filtered, washed with ice water until obtaining pH 7 of the filtrate. The residue was air-dried and then dried in a desiccator. Output of carbopentoxysulfanilic acid chloride amounted to approximately 100%.

III. Synthesis of (2,6-dichlorophenyl)amide of Carbopentoxysulfanilic Acid 6.2 g (0.0203 mol) of carbopentoxysulfanilic acid chloride were added portion-wise at a temperature of 85C to a mixture of 2.2 g (0.0136 mol) of 2,6-dichloroaniline and 3.23 g (0.0406 mol) of pyridine. Then the reaction mass was stirred for 45 minutes at a temperature of 80° C. Then 20 ml of hot water were added to the mass, the mixture was acidified with hydrochloric acid until obtaining pH 3-4 and cooled down to room temperature. The obtained residue was filtered, washed with water until the odor of pyridine disappeared and then dried. After recrystallization from 80% ethanol the output of target product amounted to 2.5 g (40% of the theoretical value).

IV. Synthesis of the Final Product—Sodium Salt of (2,6-dichlorophenyl)amide of Carbopentoxysulfanilic Acid 0.232 g of caustic soda were dissolved in 5 ml of ethyl alcohol (abs.) and 2.5 g of (2,6-dichlorophenyl)amide of carbopentoxysulfanilic acid were dissolved in 30 ml of ethyl alcohol (abs.). Then the two solutions were mixed and stirred for 20 minutes. After that the ethyl alcohol was distilled off under vacuum. The remaining residue was dried. The output of product amounted to 2.1 g (80% of the theoretical value).

Synthesis of potassium and ammonium salts is performed in a similar way.

Individuality of the substances was proved by means of the thin-layer chromatography method at Silufol UV-254 plates, eluent carbon tetrachloride—isopropanol=2:1. The structure of synthesized substances was proved by means of PMR spectroscopy method.

Antiviral activity of the inventive substance was determined using the model of pneumonia in white mice caused by type I herpes simplex virus.

Herpes simplex virus of type I (strain EC) was accumulated in Vero cells cultured in MEM medium with the addition of 0.2% bovine serum, 50 µg/ml of gentamicin. Virus titration was performed on Vero cells cultured in 96-well plates. Results were recorded after a pronounced cytopathic effect (CPE) appeared in virus control. The degree of intactness of the cellular monolayer was assessed visually, virus titer was calculated as the reciprocal value of Briggs logarithm of the largest dilution of the source material that is still able to produce visually notable manifestations of CPE in the cell culture (CTD50).

For assessing the virus inhibiting action of the preparations, white non-pedigree mice weighing 12-15 g ("Rappolovo" farm, Leningrad Region) were infected intranasally under a light ether anaesthesia with the herpes simplex virus in the dosage of 106 (CTD50)/0.05 ml. The preparation under study was administered intragastrically in the dosage of 50 mg/kg of weight according to a medical-preventive scheme (24 h and 1 h prior to infection, and 24 h and 48 h after the animals were infected). On day 3 the lungs of the infected animals were removed, homogenized in the presence of 10-fold volume of phosphate buffer and then 10-fold dilutions from 10-1 to 10-6 were prepared thereof. Dilutions of the lungs homogenate were used for infecting the intact culture of Vero cells and for titration of virus progeny. Positive reference was represented by lungs of mice that instead of the studied preparation received physiological solution by intragastric administration, whereas negative reference was represented by lungs of mice that received aciclovir in the dosage of 50 mg/kg of weight according to the same scheme. Each experimental group consisted of 10 animals.

The lung material was also subjected to histologic examination.

The data provided in Table 2 show that the preparation has a statistically significant virus-inhibitory activity at the model of herpetic pneumonia in vivo, and surpasses aciclovir with the same dosage.

Determining Activity Against Herpes Viruses of Type 1 and 11.

Herpes simplex virus (strain EC) was grown in Vero cells cultured in MEM medium with the addition of 0.2% bovine serum and 50 mg/l of the preparations under study.

It has been thus determined that the antiviral activity of the inventive substance significantly exceeds that of the aciclovir, in particular against the herpes virus of type II.

The inventive substance can be contained in tablets or in capsules, or in suppositories, or in drops, or in mixtures, or in ointments, creams or other forms for application to the skin and mucosae, or in an oral-buccal film, or in a spray, or in a liquid for parenteral administration, or in chewing gum.

The inventive substance manifests practically identical antiviral activity with X=Na, K or $NH_4$.

INDUSTRIAL APPLICABILITY

The invention can be implemented by means of known materials and equipment. In applicant's opinion, this enables to conclude that the inventions conform to the criterion "Industrial Applicability" (IA).

Physical and chemical characteristics of the target compounds

TABLE 1

| X | Tmelting, °C. | PMR spectrum, ppm | | | |
|---|---|---|---|---|---|
| | | NH | Ar | $OCH_2$ | $CH_3$, $CH_2$ |
| Na (I) | 120 | 9.75; 9.9 | 7.2-7.7 | 4.1 | 0.9; 1.38; 1.62 |
| K (II) | 123 | 9.8; 10.0 | 7.3-7.8 | 4.15 | 0.94; 1.42; 1.65 |
| $NH_4$* (III) | 110 (decomp.) | *) | *) | 4.2 | 0.91; 1.40; 1.63 |

*) The region of PMR spectrum of ammonium salt in low field (>7 ppm) is not characteristic: one wide signal is observed, which is caused by the formation of strong hydrogen bonds in the solution.

Results of Virus Titration

TABLE 2

| Preparation | Virus titer in lungs of mice on day 3 after the infection, Lg $CTD_{50}$ |
|---|---|
| Reference | 3.6 ± 0.15 |
| The inventive substance | 1.0 ± 0.11 |
| Aciclovir | 1.4 ± 0.34 |

Morphometric Indicators of the Pathological Process Dynamics in Lungs of Infected Animals in the Context of Application of Chemotherapeutic Agents at Different Time Stages of Herpetic Pneumonia

TABLE 3

| Preparation | Term опята ??? (in days) | Number of inflammation foci in one animal | Area of an inflammation focus in section |
|---|---|---|---|
| Reference | 2 | 10 | 76 ± 5.9 |
| | 4 | 10 | 405 ± 111.3 |
| | 6 | 10 | 343 ± 47.5 |
| Aciclovir | 2 | 8 | 55 ± 9.4 |
| | 4 | 3 | 58 ± 14.7 |
| | 6 | 3 | 24 ± 6.4 |
| The inventive substance | 2 | 3 | 47 ± 7.3 |
| | 4 | 2 | 49 ± 12.1 |
| | 6 | 1 | 14 ± 5.5 |

Antiviral Activity

TABLE 4

| | Number (%) of unaltered cells | |
|---|---|---|
| Preparation | Herpes virus of type I | Herpes virus of type II |
| Reference (non-infected cells) | 10000 (100%) | 10000 (100%) |
| Aciclovir | 7000 (65%) | 7000 (70%) |
| The inventive substance | 8000 (80%) | 9000 (90%) |

The invention claimed is:

1. A pharmaceutical dosage form comprising a compound which is a (2,6-dichlorophenyl)amide salt of carbopentoxysulfanilic acid of general formula:

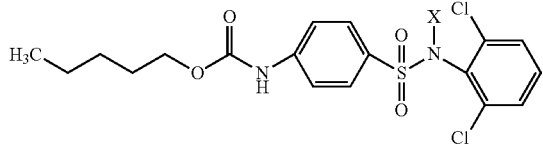

wherein said compound is present in the dosage form in an amount effective for treating a herpes virus infection; and wherein X is K or $NH_4$.

2. The pharmaceutical dosage form of claim 1, wherein X is K.

3. The pharmaceutical dosage form of claim 1, wherein X is $NH_4$.

4. The pharmaceutical dosage form of claim 1, wherein said dosage form is selected from the group consisting of a tablet, a capsule, a suppository, drops, a mixture, an ointment, a cream, a film, a spray, a liquid for parenteral administration, and a chewing gum.

5. The pharmaceutical dosage form of claim 1, wherein the herpes virus is herpes simplex virus type 1.

6. The pharmaceutical dosage form of claim 1, wherein the herpes virus is herpes simplex virus type 2.

7. The pharmaceutical dosage form of claim 1, wherein said compound is produced by a process of combining (2,6-dichlorophenyl)amide of carbopentoxysulfanilic acid with XOH, wherein X is K.

8. The pharmaceutical dosage form of claim 1, wherein said compound is produced by a process of combining (2,6-dichlorophenyl)amide of carbopentoxysulfanilic acid with XOH, wherein X is $NH_4$.

9. The pharmaceutical dosage form of claim 1, wherein said compound comprises at least 0.05% (w/v) of said dosage form.

10. A pharmaceutical composition comprising a compound which is a (2,6-dichlorophenyl)amide salt of carbopentoxysulfanilic acid of general formula:

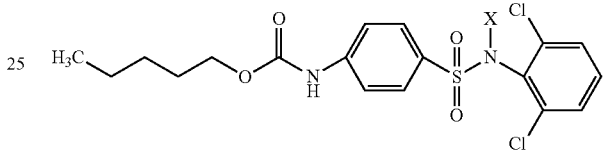

wherein X is K or $NH_4$.

11. The pharmaceutical composition of claim 10, wherein X is K.

12. The pharmaceutical composition of claim 10, wherein X is $NH_4$.

13. The pharmaceutical composition of claim 10, wherein said compound is produced by a process of combining (2,6-dichlorophenyl)amide of carbopentoxysulfanilic acid with XOH, wherein X is K or $NH_4$.

14. The pharmaceutical composition of claim 10, wherein said compound comprises at least 0.05% (w/v) of said composition.

15. A method for treating a disease caused by a herpes virus in a subject in need thereof, said method comprising administering to said subject the dosage form of claim 1.

16. The method of claim 15, wherein said dosage form is administered to said subject at least two times.

17. A method for treating a disease caused by a herpes virus in a subject in need thereof, said method comprising administering to said subject the composition of claim 10, wherein said composition is administered in an amount effective for treating a herpes virus infection.

18. The method of claim 17, wherein said composition is administered to said subject at least two times.

19. The method of claim 17, wherein the herpes virus is herpes simplex virus type 1.

20. The method of claim 17, wherein the herpes virus is herpes simplex virus type 2.

* * * * *